United States Patent [19]

Scott

[11] 4,354,064

[45] Oct. 12, 1982

[54] VIBRATORY AID FOR PRESBYCUSIS

[75] Inventor: Brian L. Scott, Denton, Tex.

[73] Assignee: Scott Instruments Company, Denton, Tex.

[21] Appl. No.: 122,011

[22] Filed: Feb. 19, 1980

[51] Int. Cl.$^3$ .......................................... H04R 25/00
[52] U.S. Cl. ...................... 179/107 BC; 179/107 FD
[58] Field of Search ...... 179/107 R, 107 BC, 107 FD

[56] References Cited

U.S. PATENT DOCUMENTS

| | | | |
|---|---|---|---|
| 1,733,605 | 10/1929 | Jones | 35/35 A |
| 1,738,289 | 12/1929 | Fletcher | 35/35 A |
| 2,432,123 | 12/1947 | Potter | 340/407 |
| 2,703,344 | 3/1955 | Anderson | 179/107 |
| 2,972,140 | 2/1961 | Hirsch | 340/407 |
| 3,157,853 | 11/1964 | Hirsch | 340/27 |
| 3,594,787 | 7/1971 | Ickes | 340/407 |
| 3,612,061 | 10/1971 | Collins | 128/418 |
| 3,699,970 | 10/1972 | Brindley et al. | 128/419 R |
| 3,766,311 | 10/1973 | Boll | 178/6 |
| 3,848,608 | 11/1974 | Leonard | 128/419 R |

OTHER PUBLICATIONS

Journal of Abnormal and Social Psychology, vol. 20, 1925 "Progress in Experiments on Interpretation of Speech by Touch" R. Gault, pp. 118–127.
Washington Star, Mar. 20, 1972 "A New Way of Hearing" J. Randal.
94th Meeting of the Acoustical Society of America, Nov. 1977, "Progress in the Development of a Tactile Aid For The Deaf" Scott et al.
Journal of Acoustical Society of America, vol. 63, No. 4, Apr. 1978, "A Method For Training And Evaluating The Reception of Ongoing Speech" Scott et al. pp. 1186–1192.

Primary Examiner—George G. Stellar
Attorney, Agent, or Firm—Richards, Harris & Medlock

[57] ABSTRACT

The present invention comprises a frequency responsive tactile stimulator. Selected mid-frequency and high frequency components are extracted from an input audio signal by a bandpass filter (18) and a high-pass filter (20). The outputs of these filters are transmitted through precision rectifiers (22, 24) and provided to modulate power drivers (26, 28). A random noise signal is generated by a noise generator (30) and limited to fixed length randomly distributed pulsed by a one-shot circuit (36). The random pulses are provided as the input to the power drivers (26, 28). The lower frequency power driver (26) drives a plurality of vibrators (42–48) which are spatially arranged on a transducer to cover a distinct area. The high frequency signal component modulates power driver (28) which drives two vibrators (50, 52) which are contiguously located to produce a punctate vibration. The use of the stimulator in accordance with the present invention together with an audio amplifier hearing aid provides the user with the ability to distinguish various high frequency signal components despite the loss of hearing for high frequency signals.

4 Claims, 2 Drawing Figures

VIBRATORY AID FOR PRESBYCUSIS

TECHNICAL FIELD

The present invention pertains to aids for the hearing impaired and more particularly to an apparatus for providing tactile stimulation to assist the user in distinguishing sounds which are similar but have differing frequency content.

BACKGROUND ART

Heretofore a wide variety of approaches have been taken to aid person suffering a hearing loss. The most commonly used device is the audio ampification hearing aid. However, for persons suffering profoundly impaired hearing, such as in presbycusis, hearing loss in the elderly, there are adverse physiological implications to the use of audio amplification as the sole aid to hearing.

In order to assist individuals suffering a hearing loss, such as due to presbycusis, added stimulation has been provided to assist audio amplification. In particular, there have been developed numerous means for stimulating the skin in response to audio signals to provide a supplementary stimuli so that the individual can better distinguish various sounds. Such stimulators have included electrodes for providing a mild electrical shock, thermal varying sensors and vibrators. In some prior art applications, the tactile stimulators are activated in response to particular frequency components of the audio signal.

Despite the development of such devices to provide skin stimulation, difficulty for the individual to distinguish certain sounds in speech which are similar in many respects but have basically different frequency components has remained a problem. An example of sounds which are difficult for hearing impaired persons to distinguish are the s sounds in the words "six" and in "shoe". Similar problems exist for other sounds of this type. Therefore, there exists a need for a tactile stimulator which enables the individual to readily distinguish between sounds which are quite similar but have fundamental frequency differences and also have fundamental differences in meaning.

DISCLOSURE OF THE INVENTION

A tactile aid is provided for use in conjunction with a conventional audio amplification hearing aid for persons having high frequency hearing loss. The tactile aid enables the individual to distinguish differing speech components which have similar characteristics. The tactile aid includes a mid-frequency filter for extracting a mid-frequency signal component from an audio signal, a high-frequency filter for extracting a high-frequency audio component from the audio signal and a circuit for generating a band-limited noise signal. A transducer is provided which has a plurality of spacially distributed vibrators for producing an areal skin response and one or more contiguous vibrators for producing a punctuate skin response. The mid-frequency signal component modulates the noise signal to produce a power signal for driving the specially distributed vibrators. The high-frequency signal component modulates the noise signal to produce a power signal for driving the contiguous vibrators for producing a punctuate response. The user can thus distinguish by skin response syllables which have different high-frequency components.

BRIEF DESCRIPTION OF DRAWINGS

For a more complete understanding of the present invention and the advantages thereof, reference is now made to the following description, taken in conjunction with the accompanying drawings, in which.

DETAILED DESCRIPTION

The present invention deals with an aid to the hearing impaired and in the usual application would be used in conjunction with a conventional audio amplifier type hearing aid. The present invention provides a unique tactile stimulation to aid the user to distinguish particular sounds which are especially difficult to discern by persons having high frequency hearing loss.

Figure 1:
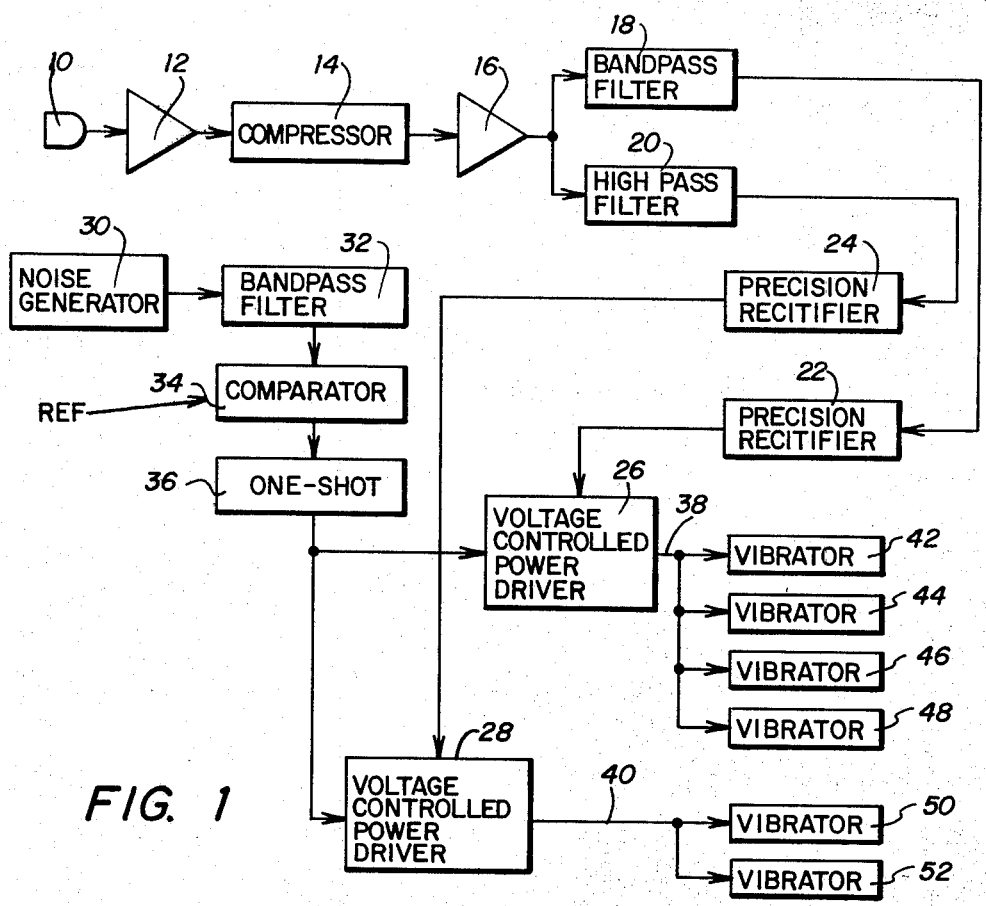
FIG. 1 is a block diagram of a tactile aid in accordance with the present invention.

The tactile aid of the present invention is described in block diagram form in reference to FIG. 1. An audio frequency sound, usually speech, is captured by a microphone 10 and transferred to a preamplifier 12 which supplies the audio signal to an audio compressor 14. Compressor 14 is of a standard type and provides frequency and amplitude limiting. The output signal of compressor 14 is transmitted to an amplifier 16 which supplies the audio signals to a bandpass filter 18 and to a high-pass filter 20. The pass band of filter 18 is centered at 2.4 kHz with a band width of 0.6 kHz. The high-pass filter 20 passes substantially all audio frequency components above 8 kHz.

The output signals from the filters 18 and 20 are transmitted respectively to precision rectifiers 22 and 24. Within rectifiers 22 and 24 the frequency limited signal components are converted to DC level signals which are used to modulate voltage controlled power drivers 26 and 28.

A random noise bi-level signal is provided as the input to the power drivers 26 and 28. This signal is generated by a series of components starting with a noise generator 30 which produces a random noise signal that is processed through a bandpass filter 32 which transmits a band width of 0.2 kHz centered at a frequency of 0.25 kHz. The band limited signal is provided to a comparator 34 which compares the incoming signal to a fixed reference DC level and generates an output signal based on this comparison. The product of the comparison operation is transmitted to a one-shot circuit 36 which generates a fixed length pulse upon receipt of an input signal from the comparator 34. The output of the one-shot comprises a train of pulses separated by random time intervals. The time intervals range from a minimum of ≃1 milliseconds to a maximum of ≃5 milliseconds. The randomly separated pulses produced by circuit 36 are provided as the inputs to the power drivers 26 and 28.

The input signals to the power drivers 26 and 28 are amplitude modulated by the outputs of precision rectifiers 22 and 24 to produce output signals on lines 38 and 40 which are proportional in amplitude to selected signal components of the audio sound supplied to microphone 10.

Line 38 is connected to a plurality of electrical vibrators 42–48 which vibrate at the rate of the input signal supplied thereto. Likewise the signal produced on line 40 is transferred to a pair of electrical vibrators 50 and 52. The vibrators 42–52 are substantially identical and are commonly used in the field of tactile sensation.

Referring to FIG. 1 for an operational description of the tactile stimulator of the present invention, an audio signal is input to a microphone 10 wherein the mid-frequency and high frequency components are extracted by filters 18 and 20. The outputs of these filters are rectified to produce control signals which modulate the power drivers 26 and 28. Random pulse signals which are generated by a noise generator and various processing circuits are provided as the input signals to the power drivers. The amplitudes of the frequency components thus extracted are utilized to modulate the random pulse noise signals. The modulated noise signals are then provided to various vibrators which respond to the signal components extracted from the input audio signal.

Figure 2:
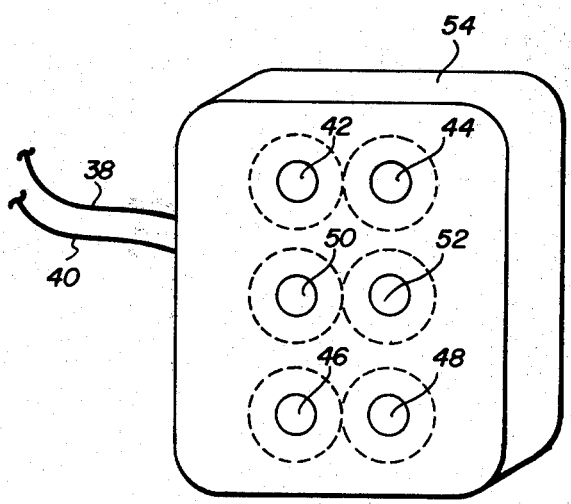
FIG. 2 is a perspective view of a tactile stimulator for use with the present invention to aid high-frequency hearing loss.

Referring now to FIG. 2, there is shown a vibratory transducer in accordance with the present invention. The lines 38 and 40 supply the output signal of the power drivers 26 and 28 respectively to the vibrators 42–52 which are mounted in the transducer 54. Note that the lower frequency signal transmitted through line 38 drives vibrators which are separated while the high-frequency signal through line 40 drives two contiguous vibrators in the center of the transducer.

The activation of the vibrators in the transducer 54 in the manner described produces a particularly beneficial result. The higher frequency signal components produce a narrow or point response referred to as a punctuate response while the lower frequency components produce a distributed wide area of response which is termed an areal response. It has been found that users can easily differentiate the punctuate from the areal response. For example, the first syllable in the word "silly" has substantial high frequency components and produces a punctuate response through operation of vibrators 50 and 52. On the other hand, a syllable such as the s in "shoe" contains lower frequency components and produces an areal response by activating vibrators 42–48.

Persons who suffer high frequency hearing loss, as in presbycusis, have great difficulty in distinguishing such sounds. But with proper training, the individual can rapidly learn to associate the punctuate response of a stimulator with the high frequency components, while associating the areal response of the widely spaced vibrators with the mid-range frequency components.

In a typical embodiment, the transducer 54 is approximately 1 inch long, ¾'s of an inch wide and 0.25 inches thick. Such a vibrator can be worn behind the ear and where it is in contact with the skin and is used in conjunction with a standard audio hearing aid.

After a period of using the tactile stimulator of the present invention, an individual suffering high-frequency hearing loss can begin to automatically recognize words spoken by others due to the type of response he receives from the transducer 54. With use over a period of time, the user generally becomes less conscious of the transducer and the understanding of various words becomes substantially automatic.

As shown in FIG. 2, the transducers are arranged in two columns and three rows in order to achieve the desired response. However, a great many more transducers can be used, or a different arrangement can be used, to produce the punctuate and areal sensations.

The present invention, therefore, serves as a tactile stimulator for use in conjunction with a conventional audio amplifier hearing aid. The circuitry of the tactile stimulator separates and isolates two frequency components of the input audio signal. These frequency components are representative of syllables and sounds which are often confused in human speech by persons having hearing impairments. The amplitudes of the selected signal components of the audio signal are utilized to modulate a power driver which receives a random noise signal from a random noise generator. The random noise signal is then audio modulated by the amplitudes of the signal envelopes of the output frequency components of filters 18 and 20. The amplitude modulated power driver signals are then transmitted to vibrators 42–52. The vibrators 42–48 respond to the signal component produced by the bandpass filter while the vibrators 50 and 52 respond to the high frequency signal component produced by filter 20. The user is thus provided with a means for distinguishing commonly used but similar sounding syllables through the generation of punctuate and areal stimulation.

Although several embodiments of the invention have been illustrated in the accompanying drawings and described in the foregoing detailed description, it will be understood that the invention is not limited to the embodiments disclosed, but is capable of numerous rearrangements, modifications and substitutions without departing from the scope of the invention.

I claim:

1. Apparatus for providing tactile stimulation to enable persons having high frequency hearing impairment to distinguish between selected frequency differing speech components, comprising:
   means for capturing an audio frequency sound to generate an audio signal;
   a compressor responsive to the audio signal to limit the frequency and amplitude thereof;
   a band pass filter connected to the output of said compressor for extracting a mid-frequency signal component of the audio signal;
   a high pass filter connected to the output of said compressor for extracting a high frequency signal component of said audio signal;
   means responsive to the output of the band pass filter to generate a first control voltage;
   means responsive to the output of the high pass filter to generate a second control voltage;
   means for generating a random noise bi-level signal;
   a first voltage controlled power driver responsive to the random noise bi-level signal and the first control voltage to produce an output signal proportional in amplitude to selected components of the audio sound;
   a second voltage controlled power driver responsive to the random noise bi-level signal and the second control voltage to produce an output signal proportional in amplitude to selected signal components of the audio sound, and
   a transducer responsive to the output signal of said first voltage controlled power driver and the output signal of said second voltage controlled power driver, said transducer having at least two spatially distributed vibrators responsive to the output signal of the first power driver for producing an areal response and at least two or contiguous vibrators responsive to the output signal of the second power driver for producing a punctuate skin response.

2. Apparatus as recited in claim 1 wherein said means for generating the first control voltage includes means for rectifying the output of the band pass filter to produce DC control voltage for modulating the bi-level noise signal, and said means for generating the second control voltage includes a rectifier to produce a DC control voltage for modulating said bi-level noise signal.

3. Apparatus as recited in claim 1 wherein said transducer has a two by three array of vibrators, the four outermost vibrators comprising said spatially distributed vibrators producing the areal response and the two interior vibrators comprising said contiguous vibrators for producing the punctuate response.

4. Apparatus as recited in claim 1 wherein said means for generating a bi-level noise signal comprises:
   a noise generator for generating a noise signal;
   a band pass filter connected to receive said noise signal to produce a band limited noise signal;
   a comparator connected to receive said band limited noise signal and produce an output pulse when said band limited noise signal corresponds to a preselected voltage; and
   a one-shot circuit connected to receive said output pulses from said comparator and generate a fixed duration pulse for each output pulse received thereby producing said bi-level noise signal.

* * * * *

UNITED STATES PATENT AND TRADEMARK OFFICE
CERTIFICATE OF CORRECTION

PATENT NO. : 4,354,064            Page 1 of 2

DATED : October 12, 1982

INVENTOR(S) : Brian L. Scott

It is certified that error appears in the above-identified patent and that said Letters Patent are hereby corrected as shown below:

Column 1, line 14, "person" should be --persons--.
Column 1, line 15 "ampification" should be --amplification--.
Column 1, line 58 "spacially" should be --spatially--.
Column 1, line 60 "punctuate" should be --punctate--.
Column 1, line 63 "specially" should be --spatially--.
Column 1, line 66 "punctuate" should be --punctate--.
Column 2, line 55 "milliseconds" should be --millisecond--.
Column 3, lines 30-31 "punctuate" should be --punctate--.
Column 3, line 34 "punctuate" should be --punctate--.
Column 3, line 37 "punctuate" should be --punctate--.
Column 3, line 45 "punctuate" should be --punctate--.
Column 3, line 66 "punctuate" should be --punctate--.

UNITED STATES PATENT AND TRADEMARK OFFICE
CERTIFICATE OF CORRECTION

PATENT NO. : 4,354,064

DATED : October 12, 1982

INVENTOR(S) : Brian L. Scott

It is certified that error appears in the above—identified patent and that said Letters Patent is hereby corrected as shown below:

Column 4, line 20      "punctuate" should be
  --punctate--.
Column 4, line 64          after "two" delete --or--.
Column 4, line 66          "punctuate" should be
  --punctate--.
Column 5, line 11      "punctuate" should be
  --punctate--.

Signed and Sealed this

Twenty-second Day of February 1983

[SEAL]

Attest:

Attesting Officer

GERALD J. MOSSINGHOFF

Commissioner of Patents and Trademarks